US00PP36860P2

(12) United States Plant Patent
Hansoti

(10) Patent No.: US PP36,860 P2
(45) Date of Patent: Jul. 22, 2025

(54) ***SANSEVIERIA* PLANT NAMED 'Hansoti57'**

(50) Latin Name: *Sansevieria trifasciata*
Varietal Denomination: Hansoti57

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,656

(22) Filed: Dec. 23, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./382
See application file for complete search history.

*Primary Examiner* — Susan McCormick Ewoldt

(57) ABSTRACT

A new and distinct cultivar of *Sansevieria* plant named 'HANSOTI57' is disclosed, characterized by foliage with a dark grey-green marginal band of 2 to 12 mm wide, occasionally up to 15 mm wide and a bright creamy yellow marginal band of 3 to 10 mm wide. Between these dark green bands is a broad band of distinctive greyed-green and cream striations. Between the green bands along the margin and the central and is a zone of bright creamy green of varying width. The new cultivar can be classified in the Compact *Sansevieria* Group type *Sansevieria* and reaches about 20 to 25 cm in height at maturity, making it a shorter cultivar in this group. Saleable plants have 7 to 9 leaves at 3 to 4 months old. The new variety is a *Sansevieria*, typically produced as an ornamental plant.

13 Drawing Sheets

Latin name of the genus and species: *Sansevieria trifasciata.*

Variety denomination: 'HANSOTI57'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI57'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI57' was discovered and selected by the inventor, Ashish Hansoti, in early to mid-2020, as a single aberrant shoot arising from a plant of *Sansevieria trifasciata* 'Hansoti20', U.S. Plant Pat. No. 30,342, at a nursery in Village Vangani, District Thane, Maharashtra State in Western India. This shoot was cut out and rooted and allowed to grow and give pups—only pups with the same characteristics of the parent were selected.

Asexual reproduction in good numbers of the new, relatively stabilised *Sansevieria* cultivar 'Hansoti57' by vegetative cuttings was started in April or May 2021 at Village Asle, District Satara, Maharashtra State in Western India and it was seen that, after a few more rounds of discarding of off-types, the distinctive combination of characteristics of the new cultivar reproduced true to type as long as the propagation was done through side shoots (basal suckers) originating from the base of the parent plant. Thus, it can be said that the new cultivar reproduces true to type through side shoots (basal suckers)

BRIEF SUMMARY OF THE INVENTION

The following traits have been repeatedly observed and are determined to be unique characteristics of 'HANSOTI57', which in combination distinguish this *Sansevieria* as a new and distinct cultivar:

1. A dark grey-green marginal band of 2 to 12 mm wide but occasionally up to 15 mm wide is one factor that distinguishes this invention from its parent 'Hansoti20'. Bright creamy yellow marginal band of 3 to 10 mm wide, equally wide on both edges of each leaf.
2. Between the above mentioned dark green bands is a broad band of grey, grey green and cream striations. This greenish-grey color is also very distinctive.
3. Between the green bands along the margin and the central band is a zone of bright creamy green of varying widths 2 to 10 mm or even more-this band substantially enhances the brightness of the leaf of this new variety.

The new variety 'HANSOTI57' is considered a variety of *Sansevieria* in the group denominated as the "Compact *Sansevieria* Group". The new variety presents an average of 7 to 9 leaves per plant when it reaches its saleable size (between 3 to 4 months from rooted liner). The new variety has a semi-erect growth habit and the entire plant can reach a height ranging between 20 and 25 cm. The leaves are of medium width (5 to 7 cm) measured at the widest part of the mature leaf under good growing conditions) and broad-lanceolate with a firm, waxy texture. The blades are thick or fleshy and slightly wavy. This variety also has an inverted triangle shape like most *Sansevieria* of the Compact Group.

The new variety is moderately drought tolerant and adapts well to conditions of bright light and moderate shade (exterior and interior).

Overall, the new variety shows a bright variegated appearance with each leaf having three distinct longitudinal bands along each leaf—the dark grey-green marginal bands of 2 to 15 mm and occasionally up to 25 mm wide along the outer edge; a broad central grey to grey-green band of striations overlaid to varying degrees by a layer of grey-cream and a bright creamy green area between these two.

Superimposed on the whole leaf is the typical *S. trifasciata* cross banding—this is prominent on the dark edge bands but also somewhat visible on the central broad band and very indistinct and barely visible on the base creamy-green areas between the edge and central band.

The marginal band along each edge of the leaf is darker grey-green, varying in width from just 2 mm to 12 mm and may be as wide as 15 mm. These marginal bands have prominent horizontal cross banding of light and dark grey-green, as is common in most *Sansevieria trifasciata* cultivars. The two colors in this band are near RHS Greyed-Green 189A and N189A.

The central area of the leaf has a wide band of various shades of grey to grey-green striations, all covered with and veiled by a thin layer of creamy grey tissue. The depth of the grey overlying tissue determines the color of these central bands-from a dark green near RHS Greyed-Green N189A to a lighter 191A or even a very light 190C.

Between these two distinct border bands is a narrow area of creamy-green. This creamy-green zone is occasionally invaded by varying amounts of bright green streaks.

The creamy-green area between the marginal and central bands therefore varies from a very narrow zone 2 mm to 10 mm wide. The color of this bright creamy-green zone is near RHS Yellow-Green 150C or N144B and lighter creamy-green zone is near 154D.

What is important to the overall look of each leaf and the whole plant is the strong contrast between the dark green border bands and this creamy green and grey-green central zone—the plant look very highly variegated and richly colored compared to other, more traditional *Sansevieria* in the "Compact *Sansevieria* Group".

Backside of the leaves is essentially the same coloring and pattern as the front with prominent dark grey-green marginal bands but somewhat narrower than on the front—typically 1 to 8 mm wide. The central band is also subdued and the creamy green tends to predominate—the overall look is a creamy green to grey-green central zone between the marginal dark green bands. On the back side of the leaf the typical *S. trifasciata* cross hatching is more visible, more prominent on the edge green bands but obvious even on the creamy areas.

PARENTAL COMPARISON

Plants of the new *Sansevieria* 'HANSOTI57' are similar to plants of the parental cultivar, however, 'HANSOTI57' differs in the characteristics described in Table I.

TABLE I

Comparison of Parental variety 'Hansoti20' (U.S. Plant Pat. No. 30,342) with new variety 'Hansoti57'

| | Characteristic | Parent *S. trifasciata* 'Hansoti20' | New cv 'Hansoti57' |
|---|---|---|---|
| 1. | Leaf & Plant Shape | Leaves are shorter and broader. Leaves, though reflexed, are more upright compared to Hansoti57. | Leaves are longer but narrower and more reflexed, so the overall plant is broader or wider in diameter. |
| 2. | Overall Color | Bright, overall creamy yellow look with central broad band of light green and streaks and bands of variable width and bright green color along edges. | Grey-Green overall look because the prominent dark grey-green bands along leaf edges and broad central band encroach into the creamy green areas. But higher level of contrast giving a rosette that looks highly variegated. |
| 3. | Border | Very variable, ill-defined, light, stippled, discontinuous band of bright green to grey green - typically around 10 mm wide but may be entirely absent or up to 25 mm wide. | Dark grey-green, prominent border, 2 to 15 mm or more wide, along both sides of leaf. The typical horizontal striations of *S. trifasciata* are very prominent here on these marginal bands. |
| 4. | Leaf Center | Broad, diffuse light grey-green band of striations overlaid with cream and surrounded by a strip of bright cream. | Central diffuse green band is broader, lighter, overlaid with more cream. Surrounding creamy-green zone is a somewhat different color, narrower, being covered to large extent by the broad central band. |

In brief, the new 'Hansoti57' presents a different color palette-grey-green and lemon yellow—compared to the overall much more golden yellow parent.

The variety 'Hansoti20' gave rise to the variety 'Hansoti57'. 'Hansoti20' shows somewhat less vigour than 'Hansoti57', typically has fewer leaves per plant (6 to 8 leaves), with a somewhat broader and shorter leaf with an average leaf width of 6 to 7 cm (measured in the middle of the mature leaf.) The growth habit is semi-erect and presents wider leaves supported in a rosette. The entire plant can reach a size from 20 to 25 cm. The plant has, as for 'Hansoti57', an inverted triangle shape. The leaves are broad-lanceolate with a waxy texture.

In comparison, 'Hansoti57' presents as a somewhat less creamy plant: the central light grey-green central band with greyish overlay is wider and the marginal bands (2 to 15 mm wide), are prominent, dark, grey-green also encroach on the cream area. These two together considerably restrict the cream area compared to the same in 'Hansoti20'. The number of leaves are also more (typically 7 to 9 leaves)

This overall difference in the amount of green in the leaf gives a distinctly different look from the parent while also increasing the cultivars growth speed and its overall vigor.

COMMERCIAL COMPARATOR

Plants of the new *Sansevieria* 'HANSOTI57' are similar to the commercial variety *Sansevieria trifasciata* 'Futura Superba', unpatented. Plants of the new *Sansevieria* 'HANSOTI57' differ from plants of the commercial cultivar in the characteristics described in Table II.

TABLE II

Comparison of well-known variety 'Futura Superba' & the new variety 'Hansoti57'

| | Characteristic | Comparable Cultivar *S. trifasciata* 'Futura Superba' | New cv 'Hansoti57' |
|---|---|---|---|
| 1. | Leaf arrangement | Very vertically oriented leaves | Much more reflexed (less erect) leaves |
| 2. | Number of leaves | 6 to 8 leaves | 7 to 9 leaves |
| 3. | Variegation Pattern | Overall Dark Green leaves with prominent transverse markings and a creamy yellow border band. | Overall grey-green leaves with broad central light grey-green band AND darker grey green border bands with creamy green variegation in between. |
| 4. | Border variegation | 2 to 15 mm wide creamy yellow band with subdued transverse banding. | 2 to 12 mm or wider dark grey-green band with prominent transverse banding. |
| 5. | Central Variegation | Green leaf with no central variegation, but with prominent transverse banding in leaf central area. | Prominent grey-green broad band in center veiled by layer of creamy tissue and with creamy green variegation on either side of this central band. Typical *S. trifasciata* transverse banding visible but not very prominent. |

BRIEF DESCRIPTION OF THE PHOTOGRAPHS

The accompanying photographs illustrate the overall appearance of the new *Sansevieria* cultivar 'HANSOTI57' showing the colors as true as is reasonably possible with colored reproductions of this type. Colors in the photographs may differ slightly from the color value cited in the detailed botanical description which accurately describe the color of 'HANSOTI57'.

These pictures illustrate the plant form which is the unique characteristic of 'HANSOTI57' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

FIG. 1, FIG. 2 and FIG. 3 show a saleable size plant of *Sansevieria* 'Hansoti57' in a 12 cm diameter pot from various angles. The photos illustrate top as well as bottom of leaves and the leaf arrangement.

FIG. 4, FIG. 5 and FIG. 6: Show different views of a tray of 'Hansoti57' with 8 plants showing uniformity across multiple plants.

FIG. 7 illustrates the three cultivars cited in this patent application pictured together for easy comparison. The new cultivar 'Hansoti57' (Top) showing an overall grey-green and cream coloration but with dark grey green edge bands. The patented parent cultivar—'Hansoti20' (Bottom Left) showing golden yellow overall colour and indistinct bright green border coloration. Finally, the old, standard cultivar 'Futura Superba' (Bottom Right) representing the classic "Compact *Sansevieria* Group" showing bigger, broader, more robust leaves and fewer leaves.

DETAILED BOTANICAL DESCRIPTION

Figure 1:
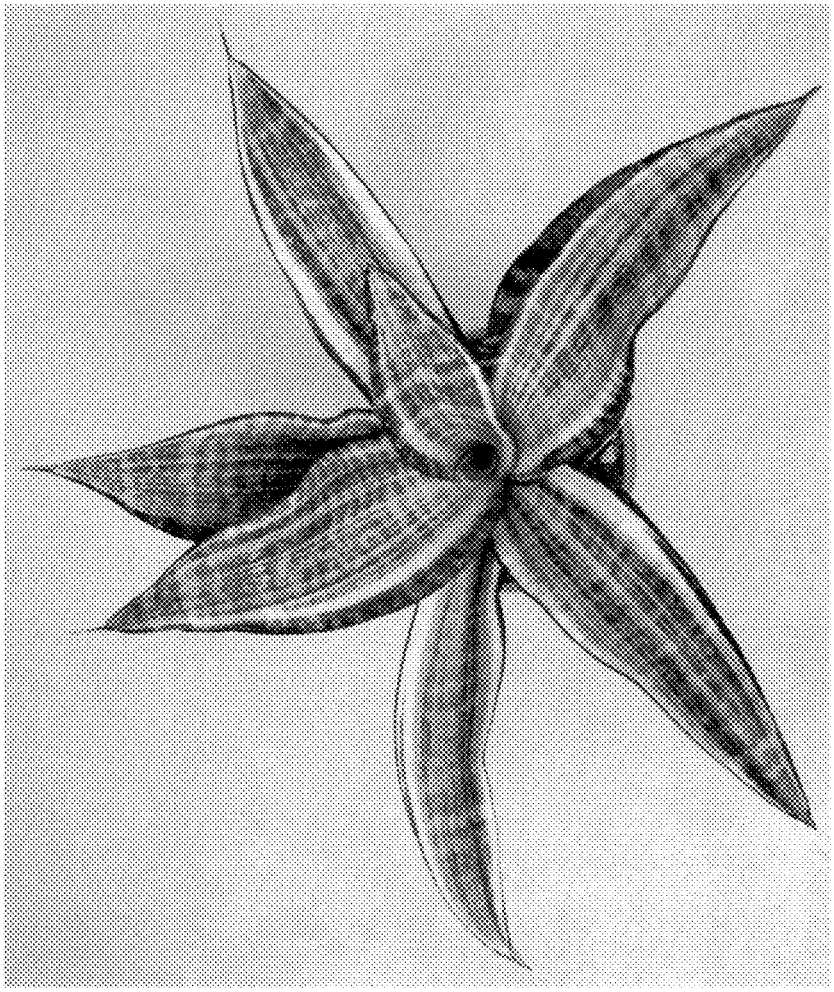
Figure 2:
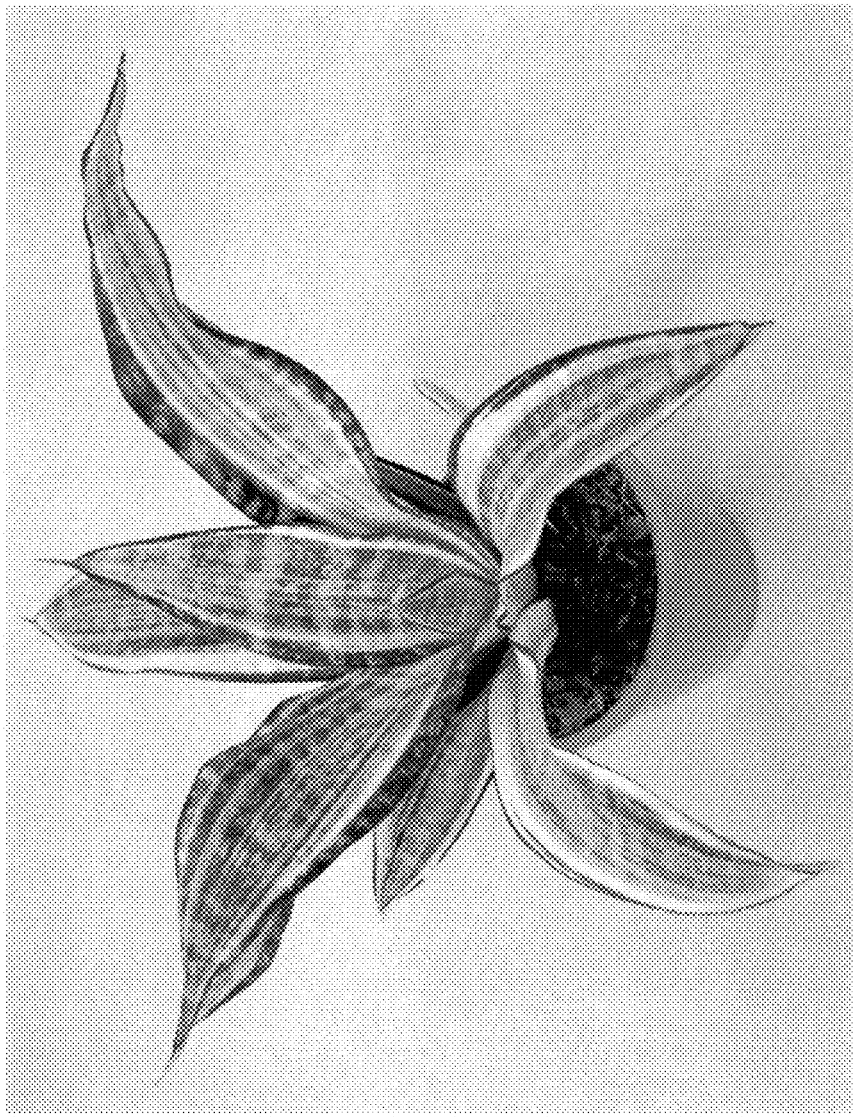
Figure 3:
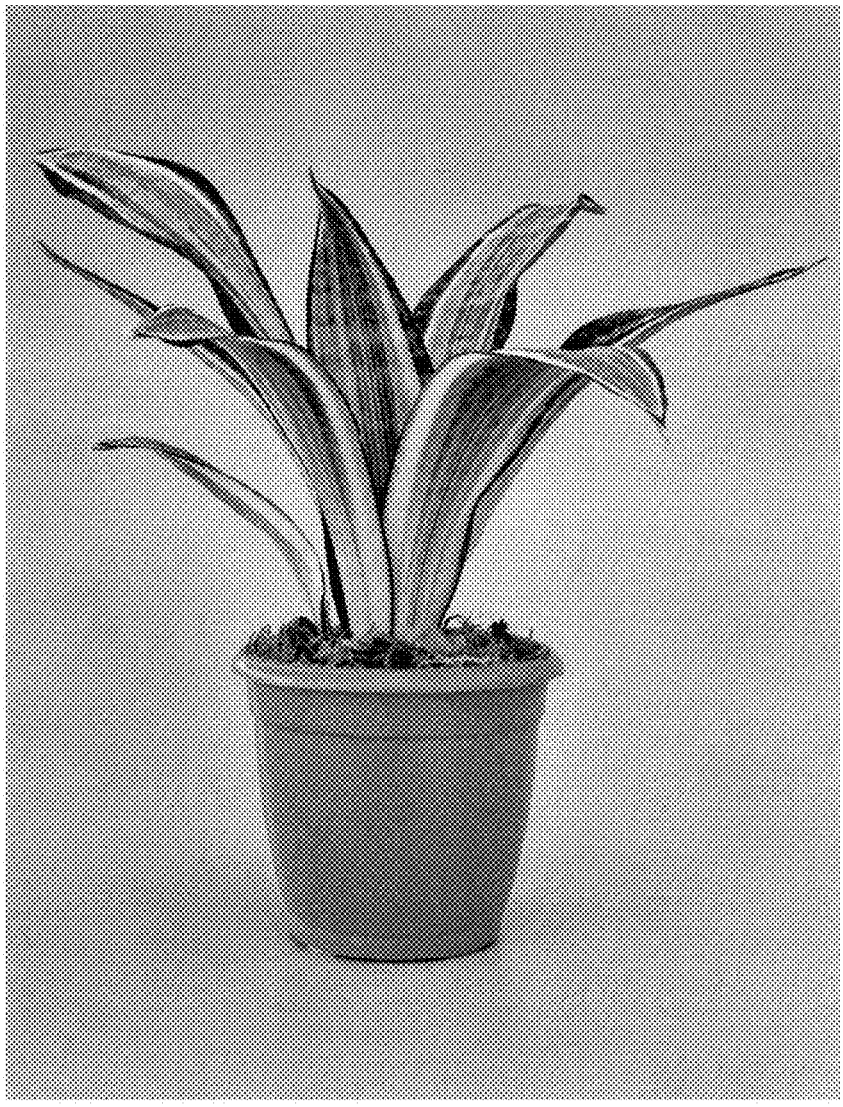
Figure 4:
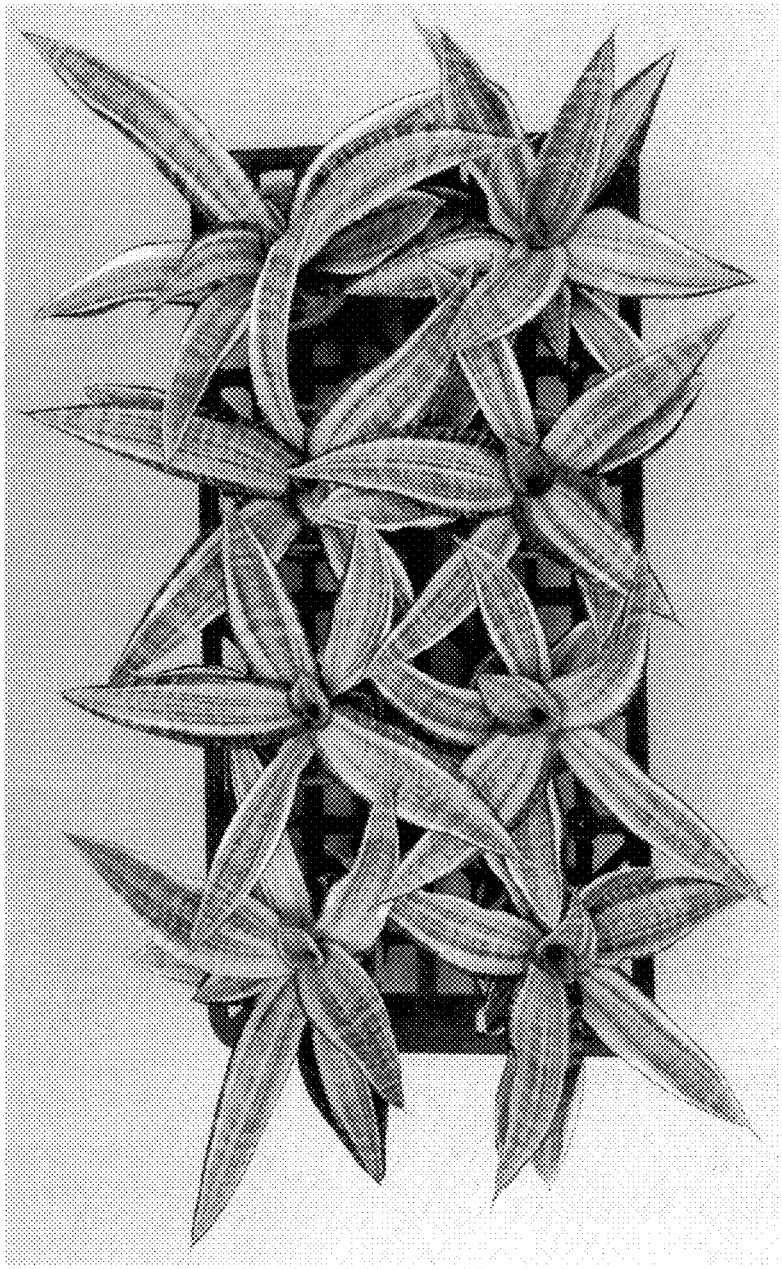
Figure 5:
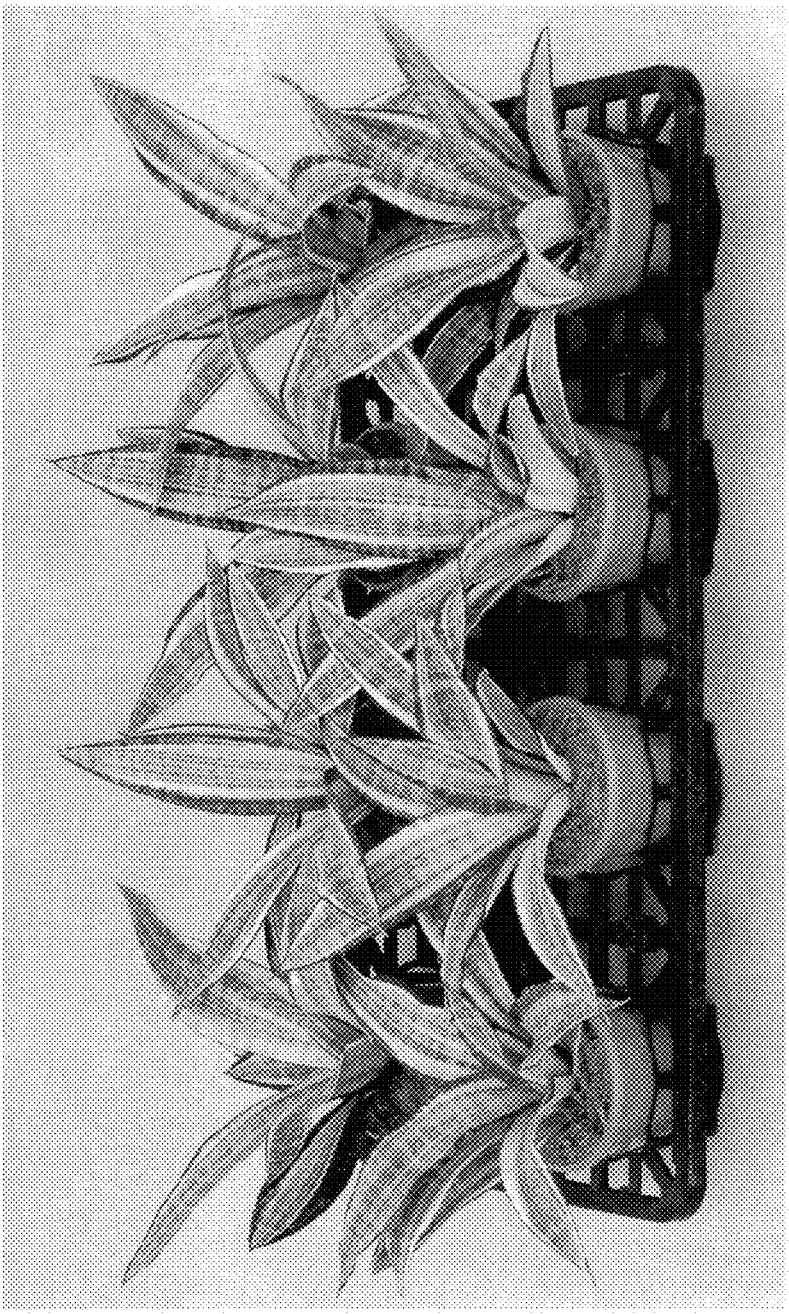
Figure 6:
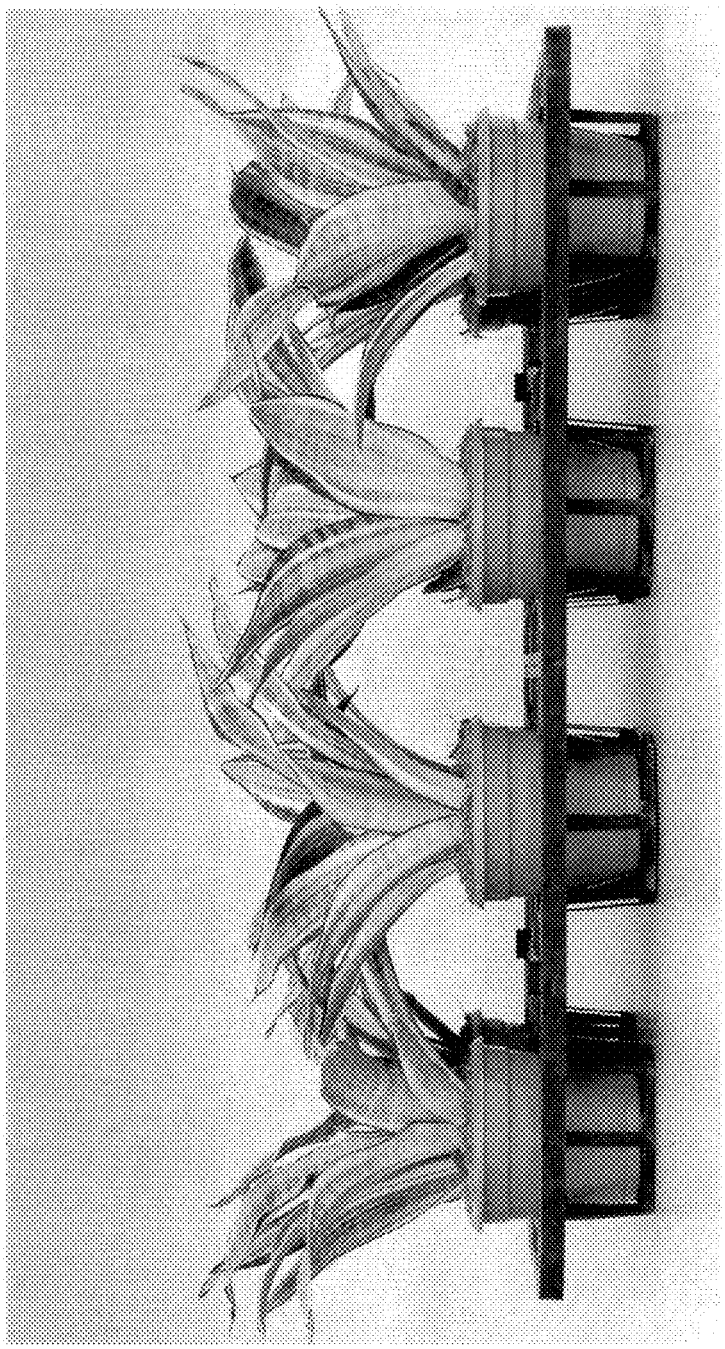
Figure 7:
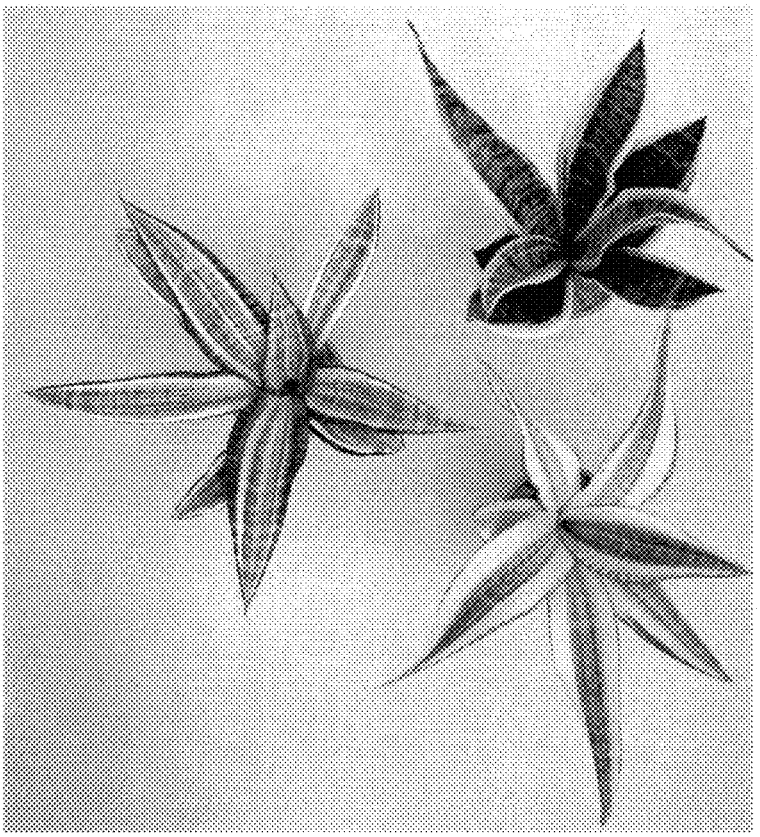
Figure 8:
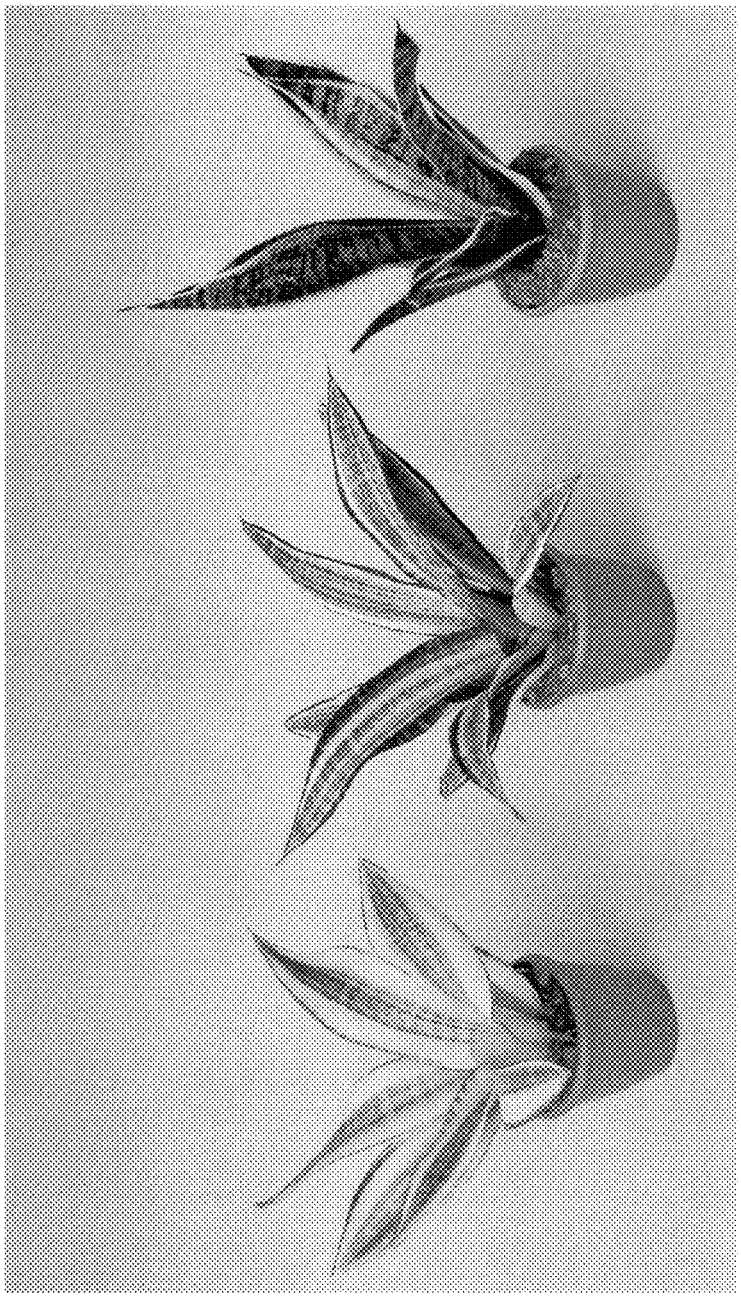
FIG. 8 illustrates the same cultivars from FIG. 7 from a different angle.
Figure 9:
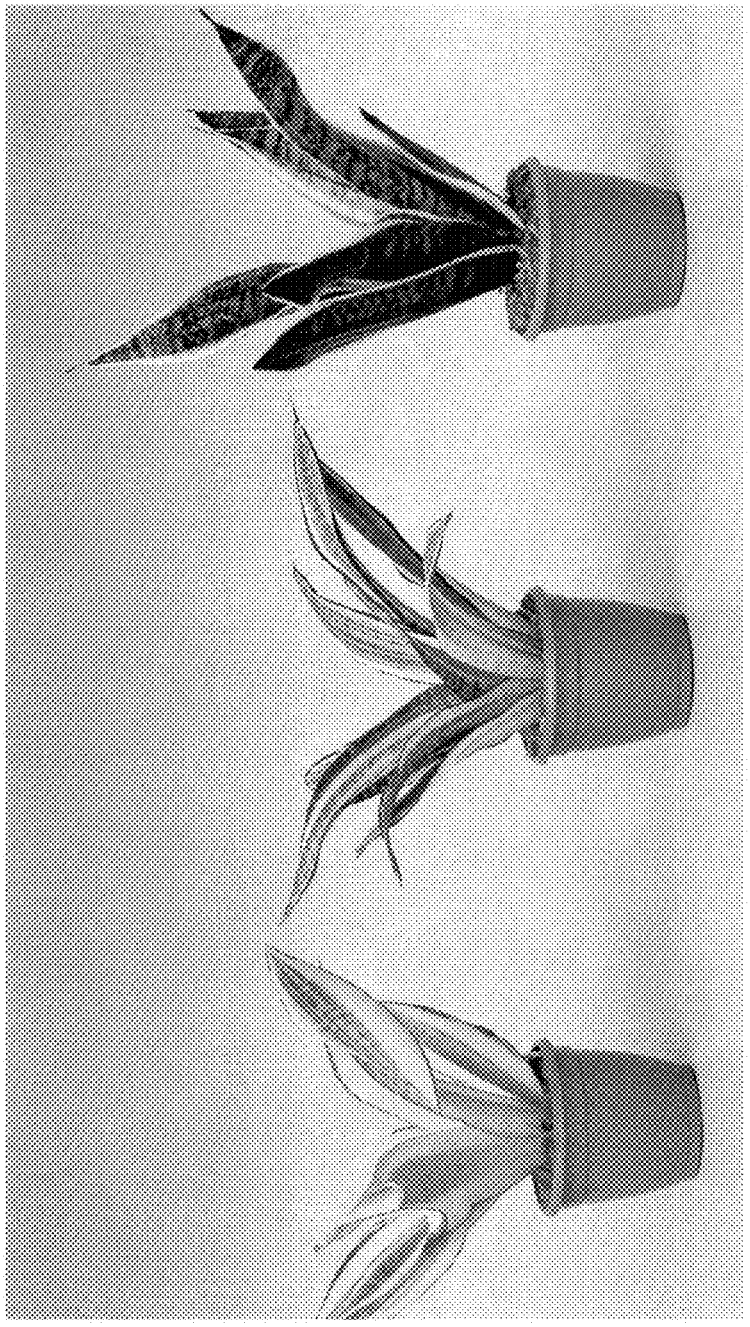
FIG. 9 illustrates the same cultivars from FIG. 8 from a side view. Leaves of Hansoti57 is even more reflexed than Hansoti20, which is more reflexed (less erect) than the "Compact *Sansevieria* Group" standard cultivar 'Futura Superba'.
Figure 10:
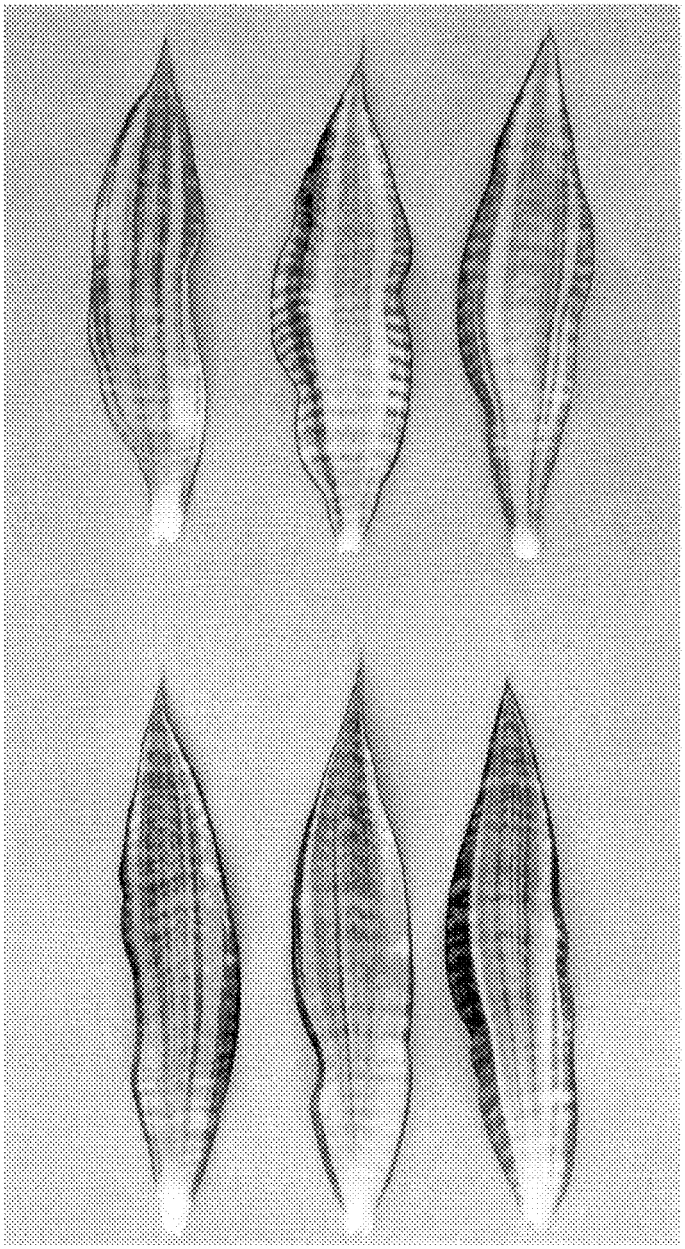
FIG. 10 shows individual leaves adaxial (top) surface of the parental variety 'Hansoti20' (Upper Row) and the new *Sansevieria* 'Hansoti57' (Bottom Row), compared to show the differences in variegation pattern and colour.
Figure 11:
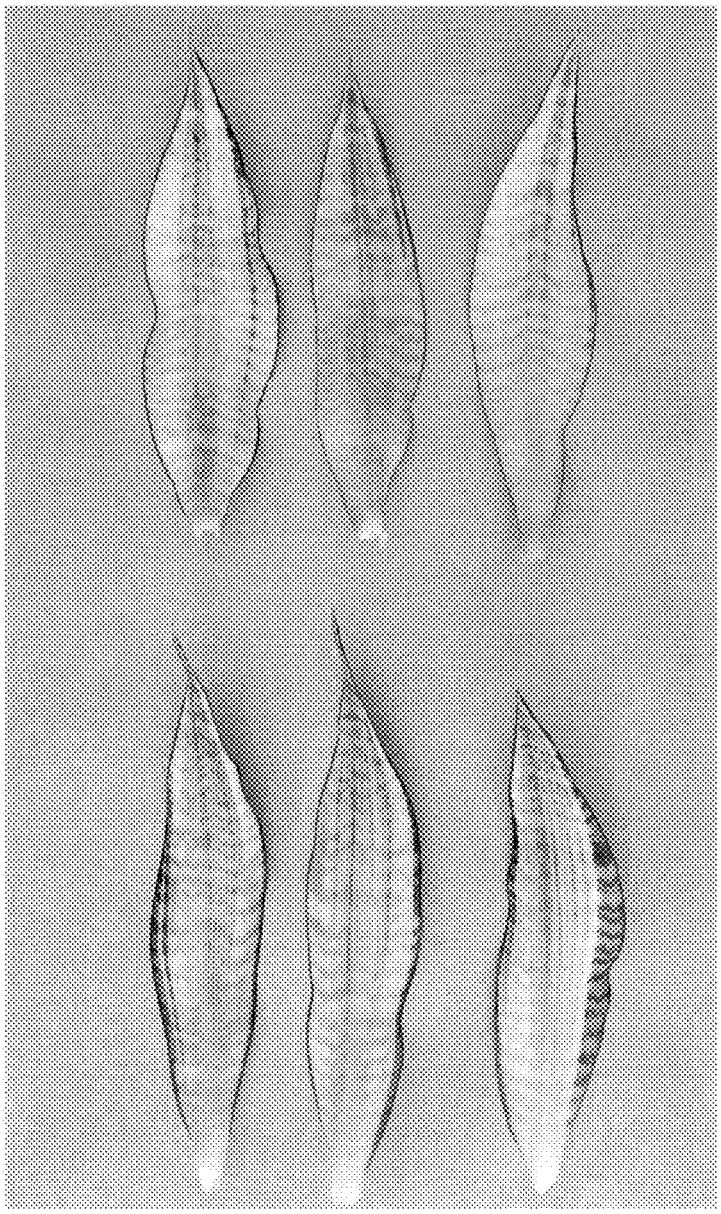
FIG. 11 shows individual leaves abaxial (bottom) surface of the parental variety 'Hansoti20' (Upper Row) and the new *Sansevieria* 'Hansoti57' (Bottom Row), compared to show the differences in variegation pattern and colour.
Figure 12:
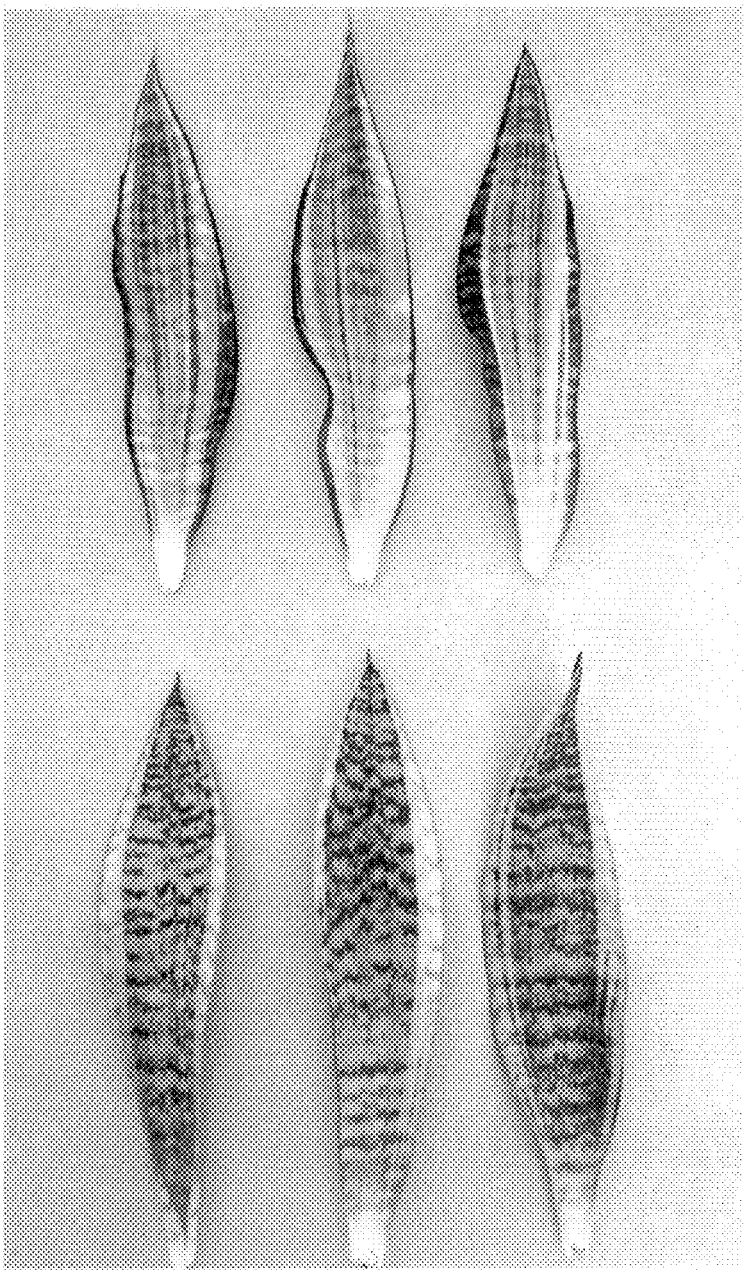
FIG. 12 shows individual leaves adaxial (top) surface of *Sansevieria* 'Hansoti57' (Top Row) and the comparison variety *S. trifasciata* 'Futura Superba' (Lower Row) compared to show the differences in variegation pattern and colour.
Figure 13:
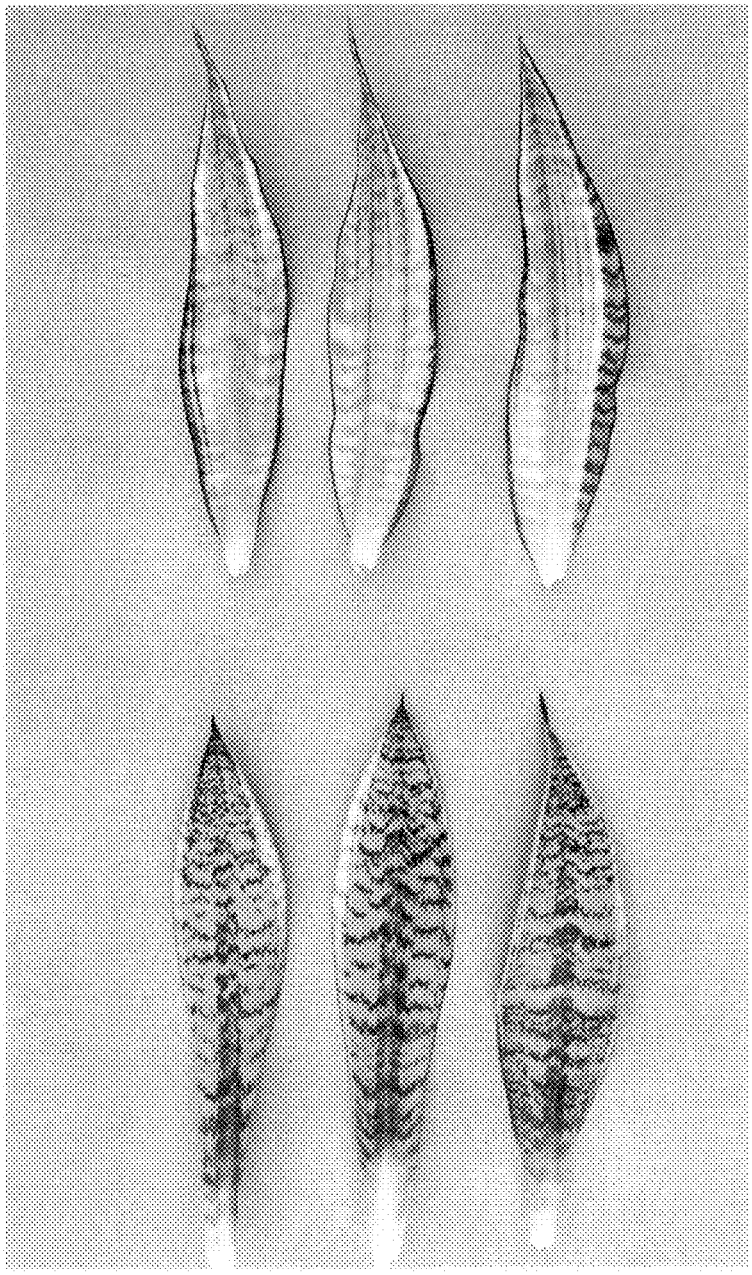
FIG. 13 shows individual leaves abaxial (bottom) surface of *Sansevieria* 'Hansoti57' (Top Row) and the comparison variety *S. trifasciata* 'Futura Superba' (Lower Row) compared to show the differences in variegation pattern and colour

The new *Sansevieria* 'HANSOTI57' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI57' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer 13:11:11, type 360-days release at 1 kilo/cubic meter of media, constant liquid feed at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2009) except where general colors of ordinary significance are used.

The photographs and descriptions were taken during the winter season in Asle, District Satara, Maharashtra State, India when outdoor day temperature was 25° C. to 30° C. and cool nights, usually of 10° C. to 15° C. The age of the plants described is 3-4 months from rooted liners.

Botanical classification: *Sansevieria trifasciata* 'HANSOTI57'.

General information:

*Parentage.*—*Sansevieria trifasciata* 'Hansoti20', U.S. Plant Pat. No. 30,342.

*Optimal growth conditions.*—

*Light intensities.*—High adaptability to outdoor or indoor conditions but needs some shade in hot climates. Shade levels of 35% to 75% depending on season to give maximum light intensity of 400 $\mu mol/m^2/s$.

*Temperature.*—Day: 25° C. to 35° C. Night: 15° C. to 25° C.

*Temperature tolerance.*—Tolerant to a low temperature of about 6° C. and a high temperature of 38° C. and above — very heat tolerant.

*Fertilization.*—Constant feed of 100 ppm N, 20 ppm P and 100 ppm K is used along with micronutrients with occasional leaching. Nutricote 13:11:11 added at 1 kg/cubic meter of growing media.

*Growth regulators.*—Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—25 to 30 days at 25° C. to 30° C.

*Time to produce a rooted liner.*—About 45 days at 25° C. to 30° C.

*Time to produce ready* 12 *cm potted plant from liner.*—About 12-15 weeks at 25° C. to 30° C.

Plant:

*General appearance and form.*—Monocot; leaf bases arranged in a rosette around growth point.

*Height.*—About 20 to 25 cm when grown in 12 cm pots.

*Spread.*—About 35 to 40 cm when grown when grown in a 12 cm size container.

*Growth rate and habit.*—Moderate; semi-upright.

*Shape.*—Inverted triangle.

*Fragrance.*—None.

*Stem.*—Modified (rhizomes with erect foliage).

*Rosette height.*—About 25 to 30 cm height from top of pot when grown in 12 cm size container.

*Rosette diameter.*—About 15 to 20 cm.

*Texture.*—Smooth, waxy.

*Color.*—As described above.

*Strength.*—Strong and durable.

*Internode length.*—About 1 to 2 mm.

Foliage:

*Quantity.*—About 8 to 10 leaves.

*Arrangement and attachment.*—Single, alternate; leaf bases arranged in a rosette around central growth point.

*Leaf length.*—About 25 to 30 cm.

*Leaf width.*—About 5 to 7 cm, occasionally a little more.

*Overall shape of leaf.*—Lanceolate.

*Apex shape.*—Acute, triangular and aristate, with soft tip.

*Base shape.*—Plane.

*Margin.*—Sharp, smooth.

*Texture.*—Upper Surface: Smooth and waxy texture.

*Texture.*—Under Surface: Smooth and waxy texture.

*Pubescence.*—None.

*Color of mature leaf.*—The depth of the green tissue determines the color of these central bands — from a dark green near RHS Grey-Green N189A to a lighter 191A or even a very light 190C. The color of this bright creamy-green zone is near Yellow-Green 150C or N144B and even going to 154D.

*Margins.*—The two colors in this band are near RHS Grey-Green 189A and N189A.

*Venation pattern.*—Longitudinal/parallel to leaf shape.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs (*Rhizoecus pritchardi*). Typical pests include *Pseudococcidae longispinus* and *Tetranychus urticae.*

*Disease resistance.*—Occasionally shows *Anthracnose* and leaf spots but largely disease — free from clean mother stock and appropriate disease mitigation measures undertaken.

*Fruit/seed production.*—No fruits/seeds detected to date.

What is claimed is:

1. A new and distinct cultivar of *Sansevieria* plant named 'HANSOTI57' as herein illustrated and described.

* * * * *

FIG. 7.01